United States Patent [19]
Grosveld

[11] Patent Number: 5,849,718
[45] Date of Patent: Dec. 15, 1998

[54] TARGETING COMPLEXES AND USE THEREOF

[75] Inventor: Franklin Grosveld, Rotterdam, Netherlands

[73] Assignee: Medical Research Council, London, United Kingdom

[21] Appl. No.: 574,702

[22] Filed: Dec. 19, 1995

[30] Foreign Application Priority Data

Dec. 19, 1994 [GB] United Kingdom .................. 9425600

[51] Int. Cl.⁶ .................................................. A61K 48/00
[52] U.S. Cl. ............................................................ 514/44
[58] Field of Search ......................... 514/44; 435/320.1, 435/240.2; 424/450, 277.1, 93.1

[56] References Cited

FOREIGN PATENT DOCUMENTS 9418317  8/1994  WIPO .
9429442  12/1994  WIPO .

OTHER PUBLICATIONS

Brown, M., et al., 1987, Cell vol. 49, pp. 603–612,"Iac Repressor Can Regulate Expression from a Hybrid SV40 Early Promotes . . . ".
Papahadiopoulos, D., 1985, Annals of the New York Academy of Sciences, vol. 446, pp. 341–348. "New Methodology for Liposome . . . ".
Orkin, S.H., et al., 1995. "Report and Recommendations of the Panel to Assess the NIH Investment in Research on Gene Therapy".
Furth et al., *Proc. Natl. Acad. Sci. U.S.A.* 91:9302–9306 (1994).
Garver et al., *Gene Ther.* 1:46–50 (1994).
Maxwell et al., *Cancer Res.* 51:4299–4304 (1991).
Maxwell et al., *Chemical Abstracts*, Abstract 113:18857, 87:189–204 (1989): *UCLA Symposium Mol. Cell. Biol. New Ser.* (*Gene Transfer Gene Ther.*) "Targeted Cell Suicide by Toxin Gene Expression".
Peterson and Tupy, *Biochem. Pharm.* 47(1): 127–128 (1994).
Robinson and Maxwell, *Hum. Gene Ther.* 6:137–143 (1994).
Smith et al., *Hum. Gene Ther.* 5:29–35 (1994).
Wu and Wu, *Biother.* 3:87–95 (1991).
Yang et al., *Hum. Gene Ther.* 6:1203–1213 (1995).

*Primary Examiner*—James Ketter
*Assistant Examiner*—Irem Yucel
*Attorney, Agent, or Firm*—Kathleen M. Williams; Banner & Witcoff

[57] ABSTRACT

The invention relates to a composition including a targeting complex containing a component of an effector system and a ligand capable of targeting a cell surface marker in association with at least one further targeting complex containiing a further component of the effector system and a ligand capable of targeting a cell surface marker which is a different cell surface marker to that targeted by at least one of the other targeting complexes, wherein the desired activity of the effector system is dependent on the selective internalization and functional cooperation of the components thereof.

8 Claims, 6 Drawing Sheets

TARGETING COMPLEXES AND USE THEREOF

FIELD OF THE INVENTION

The present invention relates to selective targeting of specific cells in cell populations or tissues in vitro or in vivo so as to obtain selective biological activity with respect to genetic material introduced into the target cell.

BACKGROUND OF THE INVENTION

Current gene therapy protocols are in need of considerable improvement before the technology becomes widely applicable for the delivery of gene sequences to host organisms or their manipulation and modulation therein (see French Anderson, Science. (1992) 256, 808–813).

Recent advances have made the technology available to achieve expression of a given transcription unit in heterologous host systems comparatively powerful. Techniques are now available which allow expression of a multiplicity of genes derived from a wide variety of cells, of varied origins including mammalian, insect, yeast and bacterial, to be expressed in a regulatable manner in cell lines grown in culture or in transgenic organisms.

Regulation can be achieved at a variety of levels, including the transcriptional level, in mRNA processing and translation and in post-translational processing of gene products. Responsiveness to a variety of natural modulator systems can be built into a transgene. For example, responsiveness to hormones can be achieved by inclusion of hormone-responsive elements in transgene promoters and enhancers (Webster et al., Cell (1989) 52, 169–178). Expression of transgenes can be influenced in a tissue-specific, integration site independent, copy number dependent manner by the inclusion of locus control regions (1cr: see Grosveld et al., Cell (1987) 51, 975–985; Blom van Assendfeld et al., Cell (1989) 56, 969–977; Greaves et al., Cell (1989) 56, 979–986). Additionally, inclusion of further control means such as recognition sequences for transcription factors of eukaryotic, including mammalian, or prokaryotic origin (Hu and Davidson, Cell, (1987), 48, p.555–566; Kakidani and Ptashne, Cell, (1988), 56, p.161–167) and regulator genes which provide means to control or modulate the expression of transgenes in response to natural hormone responsive mechanisms such as glucocorticoids (Picard et al., Cell (1988) 54, 1073–1080), estrogen (Boehmelt et al., EMBO J. (1992) 11, 4641–4652) or well-characterised orally active non-toxic small molecules such as tetracycline (Gatz and Quail, PNAS, (1988), 85, p.1394–1397; Gossen and Bujard, PNAS (1992) 89, 5547–5553) may be employed to enable further regulatory control.

One of the major problems associated with present technology relates to the delivery of DNA constructs to the target cell of choice. For example, viral vectors derived from viruses such as retrovirus, adenovirus and parvovirus, at present the vectors of choice, will deliver gene constructs to many cells and tissues, but uptake is dependent on the presence or otherwise of specific viral receptors on the cell surface. Since these receptors are present on many different cell types, cell or tissue specific expression of heterologous genes carried by such viral vectors requires additional manipulations, for example (i) through the selection of cell populations ex vivo so as to separate the target cells from a complex mixture of cells; (ii) by the inclusion of gene regulatory elements capable of directing cell or tissue specific expression of the gene(s) of choice; or (iii) deletion of viral components which determine cell attachment and the incorporation on the viral coat protein of ligands which direct cell or tissue specific uptake.

Receptor mediated DNA delivery systems provide an alternative to viral vectors for the delivery of gene constructs to cells and tissues. Such a system was first described by Wu and co-workers, who developed methodology for the transfer of DNA into cells in a directed manner by means of receptor mediated endocytosis both in vitro (Wu and Wu, J. Biol.Chem.(1987) 262, 4429–4432) and in vivo (Wu et al., J. Biol. Chem. (1989) 264, 16985–16987). The system was developed for hepatocytes and took advantage of the presence on hepatocytes of receptors which bind asyloglycoproteins, which are then taken up into cells by receptor mediated endocytosis. Linkage of the glycoprotein to DNA was via polylysine covalently attached to the glycoprotein. The addition of DNA to the glycoprotein/polylysine complex resulted in a soluble complex, which could be added directly to cells in culture, or injected intravenously for delivery to, and uptake by hepatocytes in the liver. Once encapsulated in endosomes within the cell, a small proportion of the complex escapes from the endosome into the cytoplasm. This escape mechanism can be enhanced by incorporation of viral escape mechanisms, such as a co-internalization system, for example that of adenovirus (Curiel el al., PNAS (1991) 8 8850–8854), or the incorporation into the ligand/polylysine/DNA complex of influenza viral peptides known to participate in endosomal escape mechanisms (Wiley and Skehel, Ann.Rev.Biochem. (1987) 56,365–394; Wagner et al., PNAS (1991) 89, 7934–7938). Once in the cytoplasm, it is presumed that the complex is broken down using mechanisms as yet not fully understood, resulting in transport of the DNA to the nucleus where gene expression is initiated.

There is now a growing body of literature in which receptor mediated approaches have been used to import DNA into cells. In addition to asyloglycoproteins, ligands include antibodies (Trubetskoy et al., Bioconjugate Chem. (1992) 3, 323–327) and factors important for growth such as transferrin (Wagner et al., PNAS (1990) 87, 3410–3414).

In common with virus based delivery systems, all ligand based delivery systems are inherently limited in their targeting specificity by the distribution of the ligand receptors on different cell types. In some instances delivery can be obtained in a cell and tissue specific manner, for example using glycoprotein ligands for the asyloglycoprotein receptor on hepatocytes. In contrast, transferrin mediated delivery systems target a wide range of replicating cells which express the transferrin receptor (Gilliland et al., PNAS (1980) 77, 4539–4543). The so-called tumour antigens are also widely expressed on normal cells and tissues, in addition to tumour tissues. Consequently, antibodies which recognise these antigens bind normal tissues in addition to tumour, thus limiting their value for example as a means to deliver genes encoding cytotoxic proteins such as toxins. The potential of various growth factors, cytokines and proteins involved in cell trafficking as targeting ligands for receptor mediated approaches is also limited by the heterogeneity of expression of their receptors on multiple cells and tissues. Thus, where specific cell surface markers are expressed on multiple cell types the utility of their specific ligand to target gene constructs, proteins, or any other covalently linked molecule to a subset of these cells is clearly limited. It is this issue which has proved the single most important limitation to the exploitation of various ligands, in particular antibodies for the delivery of therapeutics. For example, inappropriate delivery of immunotoxins has lead to adverse side effects in the clinic.

The concept of co-transfection, selection and expression of two or more vectors into a single cell type is well documented. Established literature examples which display measurable biological effects are numerous and include the characterisation of protein:protein interactions (Field and Song, Nature, (1989) 340, p. 245–246; Chien et al., PNAS (1991) 88, p9578–9582), the analysis of transcription factor functional domains (Sadowski et al., Nature, (1988), 355, p.563–564; Webster et al., Op. Cit.) and the formation of enzyme and enzyme inhibitor complexes (Mariani et al., Nature, (1992) 357, p.384–387).

One object of the invention is to provide specificity of transfection for a cell type which lacks a cell-specific marker in a given population of cells.

Another object of the invention is to provide a method for the cell-specific targeting and expression of an effector system, for example, including a structural gene encoding a desired peptide, in the absence of an entirely cell-specific marker for the target cell.

Yet another object of the invention is to produce a desired biological activity in a selected host cell by introducing functionally interdependent components of an effector system, the functional cooperation of which results in the desired biological activity.

Another object of the invention is to provide for increased specificity of cell targeting by requiring both functional cooperation of effector system components to produce a biological activity while also requiring plural specificities for host cell targeting.

SUMMARY OF THE INVENTION

The invention seeks to address the issue of cell or tissue specific targeting through the delivery of a plurality of, i.e., two or more, components of an effector system, each component of which must be delivered by a different targeting ligand to a common target cell of choice in order to produce the desired effect. Individually, each ligand may show diverse cell or tissue specificity, but the combined specificities of all the ligands must be unique to the cell or tissue of choice, except in circumstances where additional commonality would produce no adverse side effects.

The invention thus encompasses a method for introducing into a target cell in a cell-specific manner an effector system, the method including contacting a population of cells comprising the target cell with a plurality of targeting complexes, wherein each targeting complex comprises a component of the effector system and a ligand capable of targeting a cell surface marker, and each cell surface marker thus targeted by the plurality of targeting complexes is a different cell surface marker to that targeted by at least one of the other targeting complexes, wherein expression of the effector system to produce a desired biological activity is dependent on the selective internalization and functional cooperation of the components thereof.

Preferably, the effector system is capable of eliciting the desired biological activity in the target cell only if all the components of the effector system found in the plurality of targeting complexes are internalized by the target cell and functionally cooperate therein.

In an alternative embodiment of the invention, the desired biological activity of the effector system is suppressed in the population of cells by the internalization and functional cooperation of all the components found in the plurality of targeting complexes. The desired biological activity is elicited in the target cell by the selective internalization of the components found in the plurality of targeting complexes such that at least one component is specifically excluded from the target cell.

It thus will be appreciated that an advantage of the invention may be achieved in two ways.

In one embodiment, the effector system will only elicit a biological effect in a target cell if at least two separate components thereof are internalized and allowed to cooperate. Because these components are targeted to different cell surface markers, they are targeted and internalized independently of each other and will only all be internalized by the specific, desired cell type which possesses all the necessary cell surface markers.

In an alternative embodiment, one component of the effector system may be broadly targeted to a population of cell types having a common cell surface marker and a second component of the effector system, which is an inhibitor of the first component, is also broadly targeted but is not delivered to a specific cell type. Therefore, the effector system will only be active in cells where one component is not internalized. The advantage of the invention is therefore achieved by targeting two widely-distributed markers, one of which is specifically absent from the target cell.

It will be apparent, therefore, that in the first embodiment the desired cell type should be the only cell type to possess the surface markers to which all the components of the effector system are targeted, while in the second embodiment the desired cell type is the only cell type not to possess the cell surface markers to which all the components are targeted.

The invention also encompasses a composition comprising a first targeting complex comprising a ligand capable of targeting a first cell surface marker and a first component of a effector system in association with a second targeting complex comprising a second ligand capable of targeting a second cell surface marker, the second cell surface marker being different from the first cell surface marker, and a second component of the effector system, wherein the desired biological activity of the effector system is dependent on the selective internalization and functional cooperation of the components thereof.

In preferred embodiments, the composition includes first, second and third targeting complexes in association with one another. In alternative embodiments of the invention, the composition may include first, second, third and fourth targeting complexes in association with one another. Thus, the invention is not limited to two associated targeting complexes, but may include a plurality of targeting complexes, providing each complex is specific for a cell surface marker which is not recognized by the other targeting complexes in the plurality, and provided each component of the effector system provided by the plurality of targeting complexes is different from the other components and complements the other components in the production of a desired biological activity.

Preferably, the plural targeting complexes of the invention are for use in the treatment of a disease.

Therefore, the invention also encompasses a kit for treatment of a disease, the kit including the above-described targeting complexes, and packaging materials therefor.

The invention also encompasses a method of making a composition for the treatment of a condition by gene therapy comprising admixing a first targeting complex comprising a first ligand which is specific for a cell-surface marker and a first component of a effector system with a second targeting complex comprising a second ligand specific for a second and different cell-surface marker and a second complementing component of the effector system, wherein the first and second targeting complexes are admixed so as to produce a biologically effective product.

Other features and advantages of the invention will be apparent from the following description, together with the drawings, and from the claims.

DESCRIPTION OF THE DRAWINGS

The invention is described below, by way of example, with reference to the drawings.

FIG. 4 is a schematic representation of the method of the invention used to express a Class II MHC heterodimer. The natural genes for the Eα- and Eβ-chains of mouse class II MHC Integral transmembrane protein are co-introduced into CD4+/CD2+ cell via respective polylysinated antibodies. Expression of the mature protein on the cell surface is monitored by indirect immunofluorescence and FACS analysis using monoclonal antibodies specific for either Eα- or Eβ-chain.

DESCRIPTION

Figure 1:
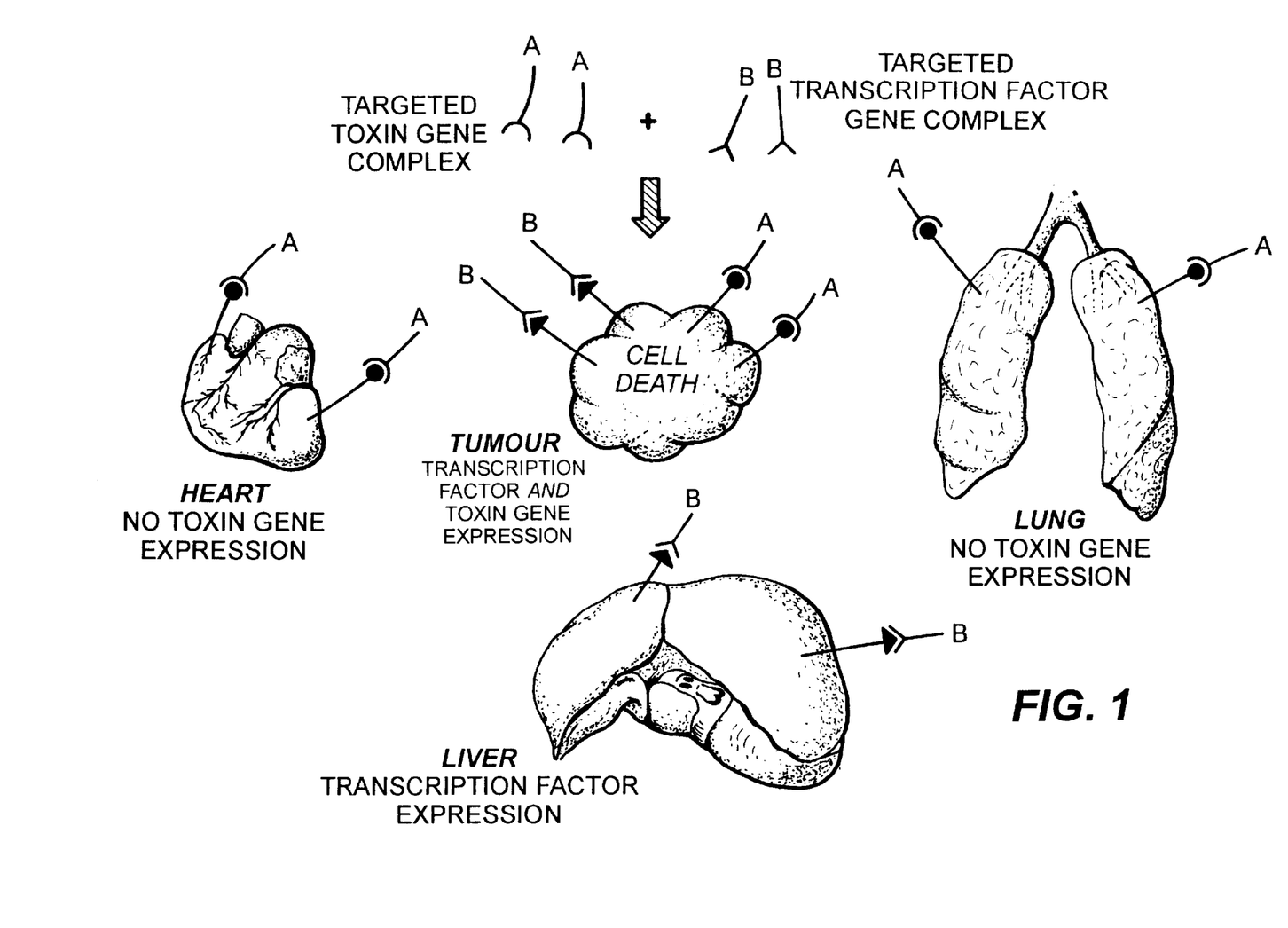
FIG. 1 is a schematic representation of the general theory surrounding the invention.

For purposes of clarifying the invention, an exemplary effector system, i.e., a two-gene system is described below and shown schematically in FIG. 1. The two-gene system is delivered to a cell via two targeting complexes which include antibodies as ligands, each antibody having specificity for a cell surface antigen on the target cell. The representative effector system includes a structural gene encoding a biologically active molecule and a regulatory gene encoding a transcription factor necessary for transcription of the structural gene.

For example, two antitumour antibodies are available, but neither shows sufficient specificity for tumour cells to warrant its use coupled to a toxin or prodrug converting enzyme due to unwanted side-effects. Antibody A may have specificity for the tumour, but also for normal heart and lung tissue, while antibody B has specificity for the tumour but also normal liver cells (see FIG. 1). Clearly, the use of antibody A or antibody B alone to deliver a toxin to the tumour would result in unwanted damage to heart and lung or liver cells. In the present invention, however, antibody A and antibody B are used together. For example, antibody A is coupled to a gene encoding a toxin and is delivered, via a receptor mediated uptake system, to tumour as well as heart and lung tissue. However, the gene is not transcribed in these cells as they lack a necessary transcription factor. Antibody B is coupled to a universally active gene encoding the transcription factor necessary for the transcription of the toxin gene and is delivered to tumour and liver cells. Therefore, in heart and lung cells only the inactive toxin gene is delivered, where it is not transcribed, leading to no adverse effects. In liver cells, the gene encoding the transcription factor is delivered and transcribed, but has no effect because no toxin gene is present. In tumour cells, however, both genes are delivered and the transcription factor can activate transcription of the toxin gene, leading to tumour-specific toxic effects.

1. Effector systems Useful According to the Invention

In the present invention, an "effector system" may be any functionality which is capable of exerting a biological effect when functional. The effector function of the effector system may be provided by proteins, nucleic acids, ions or other biologically active molecules. For example, the effector function may be provided directly by one or more proteins, nucleic acids or other molecules capable of eliciting a biological effect which are incorporated in the targeting complexes. Preferably, the effector system includes two genes, one being a structural gene encoding a biologically active product, the other being a regulator gene which regulates the activity of the structural gene. By "regulates" is meant activates or inhibits. Therefore, for the effector system to be operative according to the invention, both genes must be present in a single cell, resulting in activation or inhibition (by the regulator gene) of the structural gene, as described above. For the inhibitory effector system to be operative in all but a selected subset of cells, i.e., the target cells, the inhibitor will be present in the majority of transfected cells, and will inhibit the structural gene; however, the target cells for purposes described herein, will not contain the inhibitor and will thus express the structural gene.

The effector system may include at least one DNA transcription unit comprising at least a first gene encoding a proteinaceous or RNA molecule capable of eliciting a biological effect. The effector product may be a protein. For example, it may be a growth factor, hormone or cytokine, an enzyme, a transcription factor, a cell surface protein or a structural protein of any kind. The polypeptide may contain one or more domains of known function, not necessarily of mammalian origin. The polypeptide may be homologous to the host cell or deficient, absent or mutated therein.

Furthermore, it is envisaged that the effector system porduct may be an RNA molecule, such as an antisense RNA molecule (Mirabelli et al., Anticancer Drug Des. (1991) 6, 647–661) or a ribozyme tailored to act in a specific manner (Cech et al., J. Biol. Chem. (1992) 267, 17479–17482).

The product of the gene is advantageously a toxin or another factor which inhibits cell growth or causes cell death.

Alternatively, it may be a factor the lack of which causes a disease or disfunction which the method of the invention seeks to overcome. For example, where the disease is cystic fibrosis the gene could encode the cystic fibrosis transmembrane regulator (CFTR) protein or any other factor which has an effect in the etiology of cystic fibrosis. Alternatively, where the disease is emphysema, the gene could function to augment a deficient $\alpha$-1 antitrypsin gene. Furthermore, the invention may be applied to selective cell ablation in cancer, the manipulation of metabolic pathways and the stimulation of the immune system through the presentation of foreign antigens or the enhancement of such presentation.

Other effector genes and gene products usful according to the invention include but are not limited to the alpha-glucocerebrosidase gene, the Bruton's thymidine kinase gene, genes encoding cytokines, such as TNF, interleukins 1–12, interferons, Fc receptor, and T-cell receptor. The DNA may also include marker genes, such as drug resistance genes, the beta-galactosidase gene, the dihydrofolate reductase gene, and the chloramphenicol acetyl transferase gene.

Thus, additional diseases treatable according to the invention include diseases stemming from a genetic deficiency or defect, for example, treatment of X-linked-gamma-globulinemia or Gaucher's disease.

In another embodiment, the gene may encode an enzyme or a ribozyme capable of modulating the activity of another molecule which may be endogenous to the cell type or administered thereto, for example by addition to a culture medium or administration to a host organism via oral or intravenous routes.

The effector system furthermore may comprise at least one regulatory function which is capable of modulating the expression of the structural gene. The biological activity provided by the effector system may be conferred by a protein, a nucleic acid, an ion or another biologically active molecule, for example, a carbohydrate constituent which is synthesized by components of the effector system and which modifies a key cellular component to render it more or less biologically active. The effector system may also include a regulatory function which could be provided by one or more DNA transcription units comprising at least one regulator gene encoding a proteinaceous or RNA molecule.

If the effector system includes a structural gene, the gene is preferably substantially inactive in all cell types to which it is delivered in absence of a regulator component of the effector system.

For example, the gene encoding a regulatory factor could encode a transcription factor which promotes transcription of the gene. Alternatively, it may encode a factor capable of activating the effector product of the gene, for example a protein or RNA enzyme capable of cleaving a proeffector to produce the active form thereof. For example, the regulator gene may encode a prodrug-activating enzyme. Alternatively, the regulator effector product could comprise a component of a protein complex wherein activity is dependent on the presence of more than one product, for example one component of a heterodimer. Alternatively, the regulator effector product could be responsible for increased specificity through inactivation of an inappropriately targeted effector product or the gene itself in inappropriate tissues through the expression in these tissues of a non-toxic inhibitor of the product or the gene.

Where the regulatory factor is a transcription factor, the gene will be under the control of a regulatory mechanism which is modulated by the transcription factor. Advantageously, the promoter sequences which direct transcription from the gene comprise a nucleic acid element responsive to the transcription factor.

The transcription factor may be a heterodimer, dependent on the association of two separate gene products for activity. Such a heterodimer may regulate the activity of an endogenous gene or of a third component of a targeting complex.

Preferably, the transcription factor will not affect the expression of genes other than the gene in any cell type to which it is delivered. This end may be achieved, for example, by the use of a transcription factor and corresponding responsive element derived from a species other than that of the host cell type. Preferably, the transcription factor is not of mammalian origin. For example, may be a yeast, bacterial or insect transcription factor, such as the LexA, Gal4 or tetracycline repressor systems.

2. Cells and Cell Populations Targeted According to the Invention

In the present invention, a "population of cells" denotes any number of cells, including a single cell, which may be the same or different. It is an advantage of the invention, however, that a specific cell may be targeted amongst a number of different cell types. Preferably, therefore, a population of cells is a mixture of cell types. For example, this could be a mixture of cell varieties in cell culture, or a mixture of cells in a heterogenous preparation derived from an animal. Preferably, a population of cell comprises a whole organism to which the targeting complexes of the invention may be administered.

In addition to those cells described above, cells targeted for in vivo or ex vivo gene transfer in accordance with the invention include any cells to which the delivery of the therapeutic gene is desired. Such cells will bear a cell surface marker for which a corresponding specific ligand is available or can be prepared to allow for cell-specific targeting according to the invention. For example, cells of the immune system such as T-cells, B-cells, and macrophages, hematopoietic cells, and dendritic cells, each cell of which bears one or more well-known cell surface receptors having corresponding ligands which may be selected for use as a targeting ligand, depending upon the selected cell. Using established technologies, stem cells may be used for gene transfer after enrichment procedures (see, for example, European Patent Applications 0 455 482 and 0 451 611, which disclose methods for separating stem cells from a population of hematopoietic cells). Alternatively, unseparated hematopoietic cells and stem cell populations may be used as a target population for DNA transfer as described herein. For example, first and second targeting ligand that are specific for different determinants on hematopoietic cells are B3/25 (A.T.C.C. CRL 8034) and T58/30 (A.T.C.C. CRL 8035). Targeting ligands that are specific for populations of T-cells may be antibodies specific for a ubiquitous T-cell surface antigen 2T8–3E10 (ATCC 8213), or an activated T-cell surface antigen (OKT9, ATCC CRL8021), in combination with a targeting ligand that is specific for T-cell subpopulations, as desired, for example, T-cell suppressor/cytotoxic subsets (OKT5, CRL8013; or OKT8, CRL8014), or, as desired in combination with a targeting ligand that is specific for peripheral T-cells (OKT1, OKT11, OKT3; CRL 8000, CCRL 8027 and CRL 8001, respectively.)

3. Targeting Complexes of the Invention

In the present invention, a "targeting complex" comprises a ligand and means for delivering a component of the effector system to a target cell through cooperation between a marker on the surface of the target cell and the ligand.

For example, a ligand-targeted liposome could be used to deliver proteins and other small molecules, as well as nucleic acids, to a target cell type. Alternatively, proteins may be coupled to ligands by techniques known in the art, or may comprise natural or artificially incorporated ligands within their structure, such as for example carbohydrate groups.

Preferably, the means for delivery of the component of the effector system is a DNA vector, in linear or circular form, which comprises the essential functional elements of the invention and may comprise additional sequences as necessary for particular applications. For example, the vector may comprise a selectable marker gene. Also included may be sequences to promote the integration of the vector into the host genome or be maintained in an episomal state and/or sequences to permit replication of the vector outside the host genome.

A vector suitable for transient as opposed to persistent expression may be a circular DNA molecule in preference to a linear DNA molecule. Preferably, such a vector comprises all structural and regulatory sequences necessary for independent replication and for expression of the functional elements of the invention.

A DNA vector according to the invention preferably comprises a functional transcription unit comprising a coding sequence and the necessary promoter and enhancer elements. The promoter may be any promoter capable of functioning in the intended host cell. It will be appreciated that the potential for regulation will be a major influence on the choice of promoter. Suitable promoters may be derived from, for example, mammalian, insect, yeast or bacterial systems.

Preferably, one vector may comprise an gene whose expression is desired and provides the effector function, while a second vector comprises a gene encoding a factor which regulates the expression of the gene.

The targeting complex may also include means for facilitating internalization of the effector system component and means for promoting the functional deployment thereof. Such means may include viral peptides known to cooperate in as yet ill-defined intracellular mechanisms which permit escape of viral particles to the cytoplasm from endosomal/lysosomal pathways (Wiley and Skehel, Ann. Rev. Biochem. (1987), 56, p.365–394) and nuclear localisation signals which enhance uptake of the effector component by the nucleus (Picard et al., Cell (1988) 54, 1073–1080).

The constituent components of the targeting complex may be held in association by a variety of means. Preferred are the polylysine complexes used to attach DNA vectors to ligands by Wu and Wu (Op. Cit.) but any attachment techniques, including the engineering of a ligand into the effector system component, may be employed. For example, proteinaceous components of the effector system may be engineered to comprise peptides or other groups which act as ligands in the process of the invention. Alternative methods of attaching components of the effector system to ligands will be apparent to those skilled in the art.

In the present invention a "ligand" is any entity capable of specific binding to the surface of a cell. For example, any molecule for which a cellular receptor exists could be used as a ligand. Such substances comprise proteins, nucleic acids, carbohydrates, sugars and metal ions. The use of altered ligand molecules having engineered specificities, including a plurality of specificities, is envisaged. Especially preferred are antibodies and antibody fragments, such as Fab, F(ab')$_2$ and Fv fragments.

In the present invention, a "cell surface marker" is any entity which is capable of cooperating with the ligand in order to functionally associate the targeting complex with the cell which possesses the marker. Typically, a cell surface marker may be a cellular receptor for a natural biological entity such as a hormone, an ion or a virus. Such a receptor may itself be a protein or a modified protein, for example having a carbohydrate group optionally attached therto. However, the cell surface marker is not limited to such groups. For example, where the ligand is an antibody, the cell surface marker may be any entity which presents an epitope which is recognisable by an antibody.

By the method of the invention, it is possible to direct expression of the gene to cell types which lack a unique marker which can be targeted by a single vector system. Because at least two vectors must be used in combination, it is possible to select a cell type on the basis of its possession of two markers. This allows an increased level of specificity to be achieved.

In cases where selection of two markers is not sufficient to allow delivery of an active gene system to the desired cell type, a three-vector system may be used wherein the activity of the gene is dependent upon the presence of components carried by each of three vectors. Thereby, the presence of three separate markers on the surface of the desired cell can be selected for.

It will be apparent that there is no theoretical limit to the number of markers which can be combined in the method of the present invention. However, the need to use ever greater numbers of vectors to deliver components of an expression system of increasing complexity will place practical limitations on the number of markers which is selected.

Additional refinements may be incorporated into the method of the invention. For example, effector and/or regulator genes advantageously comprise a regulatory element capable of influencing cell or tissue specific expression. For instance, the gene and/or the regulator gene may comprise a locus control region (lcr).

Alternatively, there may be included in the expression system a regulator mechanism which provides means to control the expression of an gene, for example in response to natural hormone mechanisms such as estrogen. Advantageously, responsiveness to non-toxic small molecules capable of oral administration, such as tetracycline, may be included. Such regulation may be achieved, for example, by the provision of a fusion protein comprising a DNA binding domain conditionally dependent on interaction with a desired factor for activation.

Furthermore, DNA vectors according to the invention may comprise features which promote splicing of the transcription product or translation thereof, post-translational modification of the gene product or any other aspect of the generation of a biologically active gene product. Still further refinements include the incorporation of features to facilitate uptake and expression of the vector DNA, which may be incorporated into the vector-ligand complex. Such features include viral peptides known to cooperate in as yet ill-defined intracellular mechanisms which permit escape to the cytoplasm from endosomal/lysosomal pathways and nuclear localisation signals which may enhance uptake of vector DNA by the nucleus (see Picard et al., Cell (1988) 54, 1073–1080)

4. Hosts Treatable According to the Invention

The method of the present invention may be applied to cell populations in vitro or, advantageously, to whole organisms in vivo. For example, the method of the invention may be applied to vertebrates such as fish and mammals, or to plants. Suitable vertebrates include for example transgenic cows and sheep in which highly tissue-specific transgene expression will be enabled to, for example, improve growth characteristics or fertility, or to produce heterologous products of commercial value which may be harvested from the animal, such as for example haemoglobin or plasma proteins and components of the immune system.

Alternatively, the method may be applied to the treatment of cells ex vivo which can later be re-introduced into a host organism. The method is particularly advantageous when it is not possible or convenient effectively to isolate a given cell type for treatment ex vivo.

In an especially preferred aspect, however, the invention is of use as a method for the treatment of a disease in the human or other animal body by the tissue-specific expression of genes having a therapeutic application. For example, the method of the invention could be used to deliver a toxin gene to a tumour such that the toxin is expressed only in the tumour, even though a single, entirely tumour specific marker is not available.

Functional Analysis of the Two Gene System a) Choice of Targeting System

The principles of the invention are best exemplified using cells in culture. The cell-lines of choice will express epitopes recognised by well characterised soluble ligands such as peptide hormones, growth factors, cytokines, lymphokines, antibodies, lectins and carbohydrate binding proteins and cell adhesion/recognition molecules.

Thus exemplary cell-lines X, Y and Z will express one or more of the markers A and B (and optionally C and D, dependent on the requirement of the targeting system for three or more vectors, or the requirement for more than one ligand targeting system to deliver a single vector, when using the two vector system). The vectors will be targeted using ligands A' and B' and optionally C' and D', which recognise markers A and B and optionally C and D respectively. For example, the following cell lines will be considered: Cell-line X expresses marker A, Cell-line Y expresses marker B, Cell-line Z expresses markers A and B.

For the purposes of demonstrating improved targeting specificity, the required cell lines can be derived from a common host cell line, such as K562 cells, HeLa cells, HepG2 cells or CHO cells. Cell lines X, Y and Z can be derived from the chosen common host cell line by transfection using techniques well known in the art with appropriate genes encoding cell surface markers A or B, or cotransfection with genes encoding both A and B. Cell surface markers A and B would be well characterised cell surface proteins having known ligands, not expressed by the cell line of choice, for example the lymphocyte markers CD2 and CD4. The latter have known natural or viral ligands, while well characterised antibodies exist which could also be used for targeting. Cloned receptors for a variety of well characterised peptide hormones, lymphokines and cytokines would provide alternative model systems.

b) Construction of Ligand/DNA Targeting Complexes

For example only, ligand polylysine DNA complexes may be constructed following modifications of procedures first described by Wu (Wu and Wu, J.Biol.Chem. (1987) 262, 4429–432) and subsequently modified by Birnstiel and coworkers (Wagner et al, PNAS (1990) 87, 3410–3414; Wagner et al., (1991) 2, 226–231). To maximise endosomal escape influenza peptides known to participate in endosomal escape mechanisms (Wiley and Skehel, Ann. Rev. Biochem. (1987) 56, 365–3940) will be modified and conjugated to polylysine as described by Wagner et al. PNAS (1992) 89, 7934–7938. The ratio of ligand polylysine and peptide polylysine per DNA targeting complex can be determined by titration on a cell-line to cell-line basis. Where appropriate lysomotropic agents such as chloroquine will be included during the subsequent transfection of cells with the targeting complexes so as to enhance endosomal escape (Cotten et al,. PNAS (1990) 87, 4033–4037).

EXAMPLE 1

Figure 3:
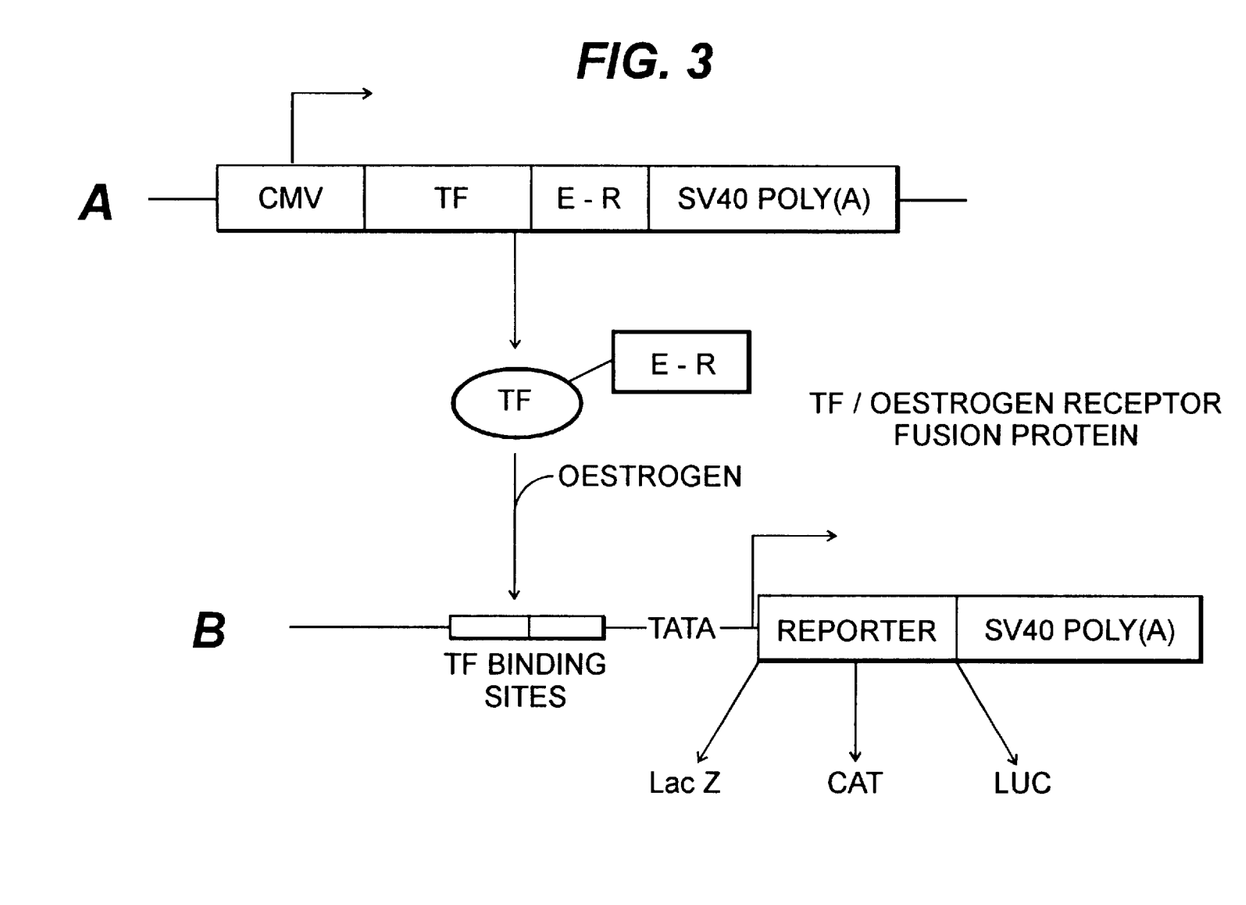
FIG. 3A is a schematic representation of the method of the invention comprising activation of a gene by a Transcription Factor/Estrogen Receptor (TF/ER) fusion protein. The same promoter (hCMV) and polyadenylation signals (SV40-polyA) as described in FIG. 2A are used to drive expression of a fusion gene consisting of the DNA binding domain of TF and the hormone binding and transcription activating domain of the ER.
FIG. 3B is a schematic representation of the method of the invention in which the TF/ER fusion protein, in the presence of estrogen, translocates to the nucleus and activates transcription from a reporter construct having one or more TF binding sites within its promoter linked to a minimal TATA box element derived from the HSV TK gene. The same set of reporter (or effector) genes are used as in FIG. 2B.

Transcriptional Activation Using a Transcription Factor/Estrogen Receptor Fusion Protein, and Targeted Transcription Therewith The experimental rationale is based on work first described by Picard et al., Cell, (1988) 54, 1073–1080, who demonstrated that if the human estrogen receptor binding domain (ER) is fused in frame to a protein of interest, that protein's activity is rendered hormone inducible. The approach has been extended by Boehmelt et al., EMBO J. (1992) 11, 4641–4652, who using the transcription factor v-rel, demonstrate that a v-rel/ER fusion protein binds NF-xB/rel sites in promoter regions and controls the expression of rel regulated genes in a hormone dependent manner. Such systems form the basis of hormonally regulatable two gene targeting systems, based on the transactivation of an gene using a regulator gene comprising a transcription factor fused to the hormone binding domain of the estrogen receptor. Thus transcriptional specificity of the gene will be determined by the incorporation of transcription factor specific binding sites and a minimal promotor just upstream of the gene (see FIG. 3).

The regulator gene DNA (transcription factor fused at the carboxy terminus to the hormone binding domain of the estrogen receptor—see FIG. 3) will be mixed with ligand B' polylys and influenza peptide polylys as described by Wagner et al, . (Wagner et al. PNAS (1992) 89, 7934–7938), to form a receptor mediated DNA targeting complex. Separately gene DNA (Binding site/minimal promotor driving a CAT gene—see FIG. 3) will be mixed with Ligand A' polylys and the influenza peptide polylys to form another receptor mediated DNA targeting complex. The targeting complexes will be then used to validate the two gene targeting system using three cell lines: cell-line Z which expresses markers A and B, cell-line X which expresses A but not marker B and cell-line Y which expresses marker B but not marker A.

CAT gene expression can be measured in all three cell lines in the presence or absence of estrogen, as a result of addition of the ligand A' gene complex or the ligand B' regulator gene complex alone or in combination to each cell-line using procedures essentially as described by Wagner et al., (Wagner et al., PNAS (1992) 89, 7934–7938).

No significant CAT activity will be measurable over background when either of the ligand A' or B' targeting complexes is incubated alone with cell-lines X, Y, or Z in the presence or absence if estrogen. No significant CAT activity over background will be observed when ligand targeting complexes A' and B' are incubated together in the presence or absence of estrogen with cell-lines X or Y. However a significant increase in CAT activity will be observed when ligand targeting complexes A' and B' are incubated together with cell-line Z in the presence of estrogen. This activity in turn will be inhibited by the presence of the anti estrogen tamoxifen.

This approach will demonstrate the successful targeting to and functional expression of both gene constructs to cell-line Z which carries markers A and B and the absence of gene expression in cell lines X and Y, which carry a single marker, A or B respectively.

Figure 2:
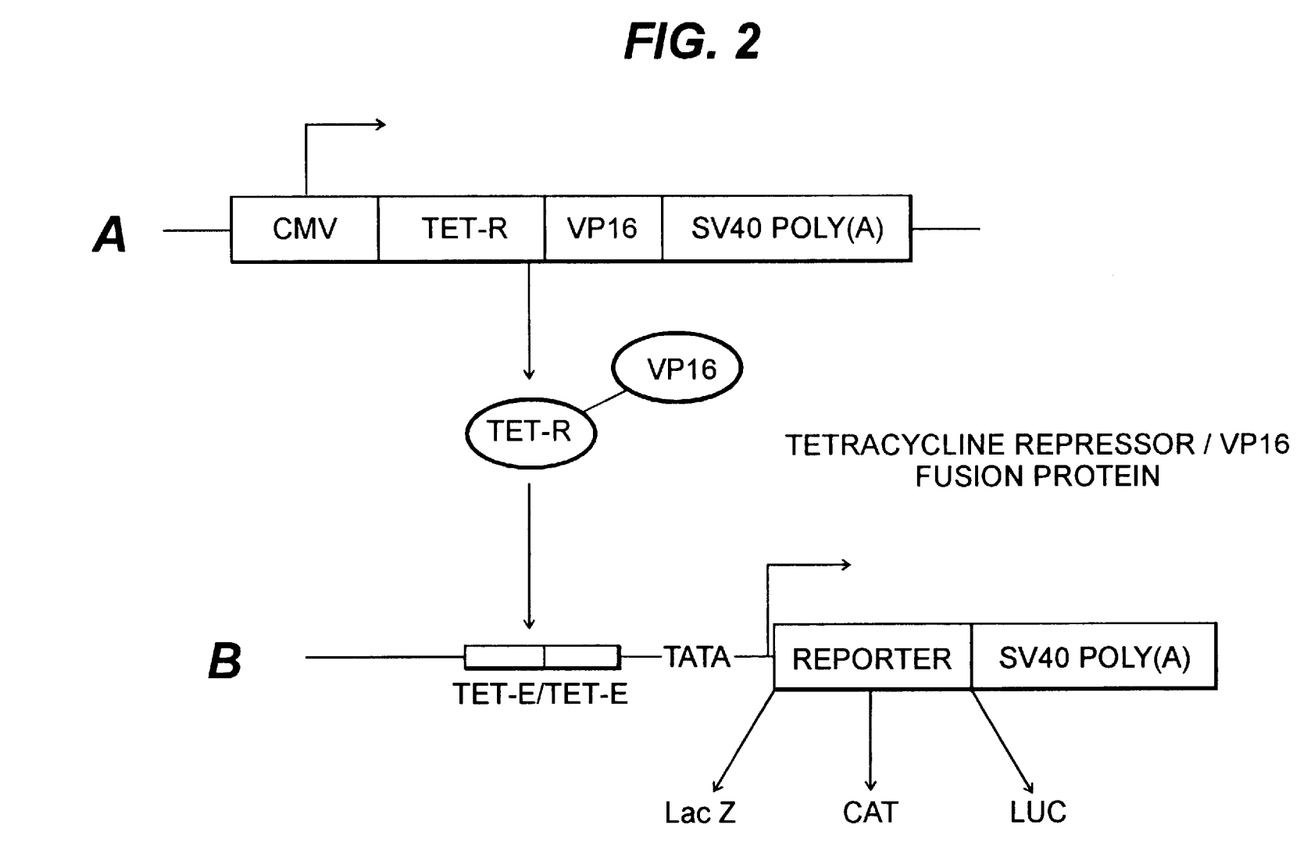
FIG. 2A is a schematic representation of the of the method of the invention comprising activation of a structural gene by a VP16/Tetracycline Repressor fusion protein (plasmid B or pB). The coding sequences for a fusion protein include the DNA binding domain from the bacterial tetracycline repressor (TET-R) and the transcriptional activation domain of the Herpes Simplex Virus VP16 protein expressed under the control of the strong ubiquitous promoter from human Cytomegalovirus (hCMV). Transcriptional termination signals for polyadenylation are derived from the large-T antigen gene of SV40.
FIG. 2B is a schematic illustration of how the TET-R/VP16 fusion protein activates transcription of a reporter construct (the luciferase gene) (plasmid A or pA) with a promoter comprising one or more binding sites for the tetracycline repressor (TET-E) linked to a TATA box from either hCMV or β-globin. A number of different reporter genes coding for easily assayable enzymes are used to quantitate levels of activation (e.g. CAT and firefly luciferase (LUC)) and transfection efficiency on a single cell basis (e.g. lacZ-β-galactosidase; anti-CAT immunofluorescence). For gene therapy, the reporter gene may be replaced with a structural gene, for example, encoding Diphtheria toxin or HSV Thymidine Kinase.

EXAMPLE 2
"Tetracycline" Suppression System, and Targeted Transcription Therewith The experimental rationale is based on the trans activation of the gene using a regulator gene comprising the Tet repressor gene (tetracycline binding protein) fused to the transcriptional activator VP16 under the control of a hCMV promoter/enhancer (see pB in FIG. 2A). Specificity is determined by the inclusion of two or more tet operator sequences upstream of a minimal human beta-globin or CMV promoter in the gene (FIG. 2) essentially as described by Bujard et al. Proc. Nat. Aca. Sci. (1992) 89, 5547–5551. The transcribed regulator gene binds the operator sequence and transactivates the reporter gene. Suppression is effected by the inclusion of tetracycline which releases the regulator gene product from the operator preventing transcriptional activation by VP16.

deprotection of the Fmoc group, using 20% piperidine in DMF, the subsequent amino acids were coupled in four fold excess using O—(1H-benzotriazo-1-yl)-tetramethyluronium tetrafluorobate (TBTU/1-hydroxybenzotriazole and N-ethyldiisopropyalmine as activating agents. After synthesis of the peptide was finished, the N-terminal Fmoc group was removed as described above to give the free amino, side chain protected, peptide bound to the resin. This was cleaved from the resin using a TFA/water/phenol/thioanisole/1,2-ethanedithiol (82.5: 5: 5: 5: 2.5) mixture. The resin was then removed by filtration. Evaporation of most of the solvent then precipitation using diethyl ether followed by centrifugation gives the crude peptide.

The crude peptide was dissolved in a small amount of 1% acetic acid in water and applied to a Sephadex G25 (superfine) column of an appropriate size and eluted using the same 1% Acetic acid solution. The fractions containing the peptide, as shown by analytical reverse phase hplc, were pooled and lyophilised. Further purification was achieved by preparative reverse phase hplc using a Dynamax 83-221-C column and a gradient of 5–30% Acetonitrile(0.1% TFA) in Water(0.1% TFA) over 20 min. The fractions containing the peptide were pooled, the acetonitrile evaporated in vacuo and lyophilised. The peptide was then desalted by dissolving it in 0.75 ml of 1% acetic acid in water and applying it to a PD-10 column which was then eluted using the same buffer. Fractions were taken every 0.75 ml and fractions 3–8 are combined and lyophilised to give the final peptide.

This peptide is used in combination with the insulin-conjugate to improve transfection efficiency.

2. Preparation of Insulin-Conjugate

The conjugate has the following structure:

Insulin-NHCO—CH2—O—N=CH—CO—KKKKKKKKKKKKKKKKKKKC—COOH
                                                          S
                                                          S
                            NH2—T—KKKKKKKKKKKKKKKKKKKC—COOH The regulator (or transactivator) gene DNA (tet-binding protein/VP16 fusion, pB) was mixed with the Insulin-lysine36 (InsII) conjugate to form a receptor-mediated targeting complex. The InsII conjugate was made as described hereinbelow.

Separately, reporter gene DNA (tet operator sequences upstream of a minimal promoter driving luciferase—see pA in FIG. 2B), is mixed with Lip2 (palmitoylated NBC-II peptide) to form a separate delivery complex capable of being taken up by many different cell types. Lip2 was made as described hereinbelow.

The complexes were then used to validate the targeting method of the invention using different cell lines, the HepG2 cell line, which is a hepatoma cell line which expresses the insulin receptor, the HeLa cell line, which is a cervical carcinoma cell line which does not express the insulin receptor, and a suspension cell line, Jurkat.

1. Synthesis of DNA Condensing Peptide NBC1

Peptide NBC1 has the following sequence:

N     H
          2
PKKKRKVEKKSPKKAKKPAK-
SAKAKAKAVKPKAAKPK
KPKKKRKVEKKSPKKAKKPAAC—COOH.

The peptide was synthesized using Millipore 9050 plus peptide synthesizer in extended synthesis cycle mode (30 min-1.25 h couplings increasing during the synthesis). Fmoc—Cys(Acm)—O—PEG—PS-Resin was used. After This insulin conjugate was prepared by reacting a periodate oxidised S-Pyridyl blocked synthetic peptide of the following structure: NH$_2$—THR—(LYS)$_{18}$—CYS—(Pyr)—COOH (Compound I) with human insulin which had been chemically modified by the introduction of a single oxime bond (Compound II) at the C-terminus of the A chain. This complex Compound II is then reacted with the free thiol form of compound I.

a) Preparation of Compound I

The peptide was synthesized using a Millipore 9050 plus peptide synthesizer in extended synthesis cycle mode (30 mins-1.25 hour couplings increasing during the synthesis). Fmoc—Cys(Acm)—O—PEG—PS-Resin was used. After deprotection of the Fmoc group, using 20% piperidine in DMF, the subsequent amino acids were coupled in four fold excess using O—(1H-benzotriazol-1-yl)-tetramethyluronium tetrafluoroborate (TBTU)/1-hydroxybenzotriazole and N,N'-diisopropylcarbodiimide as activating agents. When necessary, a four fold excess of the amino acid, O—(1H-7-aza-benzotriazol-1-yl)-tetramethyloronium hexafluorophosphate and diisopropylethylamine was used to ensure complete coupling to the growing peptide. After the synthesis of the peptide was completed, the N-terminal Fmoc group was removed as described above to give the free amino side chain protected peptide bound to the resin. This was cleaved from the resin using a TFA/water/phenol/thioanisole/1,2-ethanedithiol (82.5: 5: 5: 5: 2/5) mixture. Following precipitation with ether and centrifugation the peptide was purified using gel filtration and reversed phase hplc to give Compound V. The S-pyridyl blocked derivative (Compound I) was prepared by the method of Carlsson et al (1978) Biochem. J. 173, 723–737.

b) Preparation of Compound III

Insulin was chemically modified according to previously described methods (pp. 43–44 of Offord, R. E. (1980) "Semisynthetic Proteins" 235 pp., Wiley, Chichester and New York), with slight modifications. Briefly, 100 mg Zn-free insulin were dissolved in 1 mL of 1M sodium bicarbonate, diluted with 4 mL dimethyl formamide and reacted with an equimolar amount (relative to protein amino groups) of the N-hydtoxysuccinimide derivative of methylsulfonylethyloxycarbonate. After 1 h incubation at room temperature, the mixture was acidified and subjected to semi preparative HPLC on a C8 column equilibrated in 0.3 ammonium sulfate, pH 2.7, using a 65–90% gradient over 25 min with a flow rate of 4 mL/min (A:0.3M (NH4) 2S04, pH 2.7 (glass electrode) with concentrated sulfuric acid. The peak corresponding to di-substituted insulin (as judged by subsequent electrospray mass spectrometry) was collected and desalted on a C18 reversed phase hplc column equilibrated in 0.1% TFA. The di-derivative obtained in such reactions is known to be preponderantly the desired Al, B29 substituted molecule. Analysis of the modified protein after overnight incubation in 50 mM DTT in water allowed identification the B-chain with only a single MSC (methlysulphonylethoxy carbonyl group (calcd., m/z 3547.8; found m/z, 3549.6±0.4), which is in agreement with the desired structure. 50 mg MSC2-insulin were then dissolved in 1 mL N-methyl-pyrrolidone and reacted with a 10-fold molar excess of Boc-aminooxyacyl (AOA) n-hydroxysuccinimide derivative (made as usual according to Vilaseca et al. (1993) Bioconjugate Chem. 4 515–520), in the presence of equimolar amounts of HOBt and of sufficient N-ethylmorpholine to bring the externally indicated pH (moist pH paper) to approx. 8. After 1 h incubation at room temperature, the reaction medium was acidified and diluted with 0.1% TFA, and the derivatized insulin isolated by semi-preparative HPLC on a C8 column equilibrated in 0.1% TFA, using a 35–45% gradient (same eluants as described above) over 20 min. The MSC groups were then cleaved under standard conditions and the material repurified on the C8 column using a 35–40% gradient over 20 mins. The final compound, BOC-AoA-insulin, was characterized by ESI-MS (calcd. M/z 5950.6; found m/z 5948.1±0.1) and was deprotected by TFA treatment (30 minutes at room temperature) just before conjugation to Compound II.

c) Preparation of Compound II

The Cys-protected peptide was oxidized as follows. The peptide was dissolved in 5- mM imidazole (Cl), pH 6.9 at a concentration of 10 mg/mL, and 0.2M methionine in water was added (as a anti-oxidant scavenger) to a 10-fold molar excess over peptide. Then 50 mM sodium periodate was added to a five-fold molar excess over peptide, and the solution allowed to stand in the dark for 5 minutes, the mixture was purified by semi-preparative HPLC on a C8 column using a gradient from 10% to 60% over 25 min. in the system 0.1% (w/v) aqueous TFA/Acetonitrile-TFA-water 900:1:100 (V/W/V).

d) Preparation of Compound IV

The isolated oxidized peptide was dissolved into a solution of 5 mg of the AoA-insulin derivative (an approx. 2-fold molar excess of peptide over insulin) made up in 0.5 mL 0.1M (ac(Na) buffer to which had been added 50 μL acetonitrile, followed by adjustment to pH 3.8 (glass electrode) with glacial acetic acid.

The conjugate was isolated after 15 h incubation at room temperature and characterized by ESI-MS (calcd. M/Z 8426.1, found m/z 8429.3±0.5). The material was isolated by semi-preparative HPLC with a 30–45% gradient from the bulk of the reaction mixture. The peak fraction was dried down in a Speed Vac.

e) Preparation of Compound VI

Compound VI was synthesized by reaction of compound IV with a 5-fold molar excess of compound V in 0.1M sodium acetate buffer pH 4.6 and 20% acetonitrile. After 3 hr at room temperature, compound VI was isolated by reversed phase hplc as described above.

3. Synthesis of Lip2

Lip2 is the n-palmitoyl derivative of a basic DNA binding peptide (NBC2) and is a potent gene delivery agent of broad cell specificity. NBC2 has the following sequence:

NBCII was prepared as follows. The peptide was synthesized using a Millipore 9050 plus peptide synthesizer in extended synthesis cycle mode (1 hour couplings). Fmoc—Cys(Acm)—O—PEG—PS-Resin was used. After deprotection of the Fmoc group, using 20% piperidine in dimethyl formamide, the subsequent amino acids were coupled in four fold excess using O—(1H-benzotriazol-1-yl)-tetramethyluronium tetrafluoroborate (TBTU)/1-hydroxybenzotriazole and N,N'-diisopropylcarbodiimide as activating agents. When necessary, a four fold excess of the amino acid, O—(1H-7-aza-benzotriazol-1-yl)-tetramethyluronium hexafluorophosphate and diisopropylethylamine was used to ensure complete coupling to the growing peptide. After the synthesis of the peptide was finished, the N-terminal Fmoc group was removed as described above to give the free amino side chain protected peptide bound to the resin. This was cleaved from the resin using a TFA/water/phenol/thioanisole/1,2-ethanedithiol (82.5: 5: 5:2.5) mixture. Following precipitation with ether and centrifugation the peptide was purified using gel filtration and cation exchange hplc to give the desired product.

N-Palmitoyl-NBC2 (Lip2)was prepared as follows. The free amino side chain protected NBC2 bound to the PEG-PS Resin was reacted with Palmitic acid N-hydroxysuccinimide ester in chloroform/methanol (4:1) at room temperature overnight. The resin was then washed with 3 further aliquots of chloroform/methanol (4:1) and dried under vacuum. The peptide w as cleaved from the resin using a TFA/water/phenol/thioanisole/1,2-ethanedithiol (82.5: 5: 5: 5: 2.5). The crude peptide was dissolved in a small amount of 1% acetic acid in water and applied to a Sephadex G25 column (superfine) of an appropriate size and eluted using the same 1% acetic acid solution. The fractions containing the peptide, as shown by analytical reverse phase hplc, were pooled and lyophilized. Further purification was achieved by preparative reverse phase hplc using a Dynamax 83-221-C column and a gradient of 5–100% Acetonitrile (0.1% TFA) in 0.1 TFA) over 20 min. The fractions containing the peptide were pooled, the acetonitrile evaporated in vacuo and lyopohilized. The peptide was desalted by dissolving it in a small amount of 1% acetic acid in water and applying to a Sephadex G15 column of an appropriate size and eluted using the same 1% acetic acid solution. The fractions containing the peptide, as shown by analytical reverse phase hplc, were pooled and lyophilized to give the final peptide preparation.

4. Transfection Experiments

The targeting complexes were assayed for their ability to transfer plasmids pA (encoding the luciferase reporter gene) and plasmid pB (encoding the transactivator) into the adherent cell lines HepG2 and HeLa and the suspension cell line Jurkat. In order to establish independently that the gene transfer delivery system was sufficiently efficient the RSV-Luc plasmid which encodes the luciferase reporter gene and requires no transactivator for expression, was used in control assays with both delivery systems. After incubation, the cells were lysed and luciferin and ATP added and the light emitted measured with a luminometer. The targeting complexes were prepared as follows.

Lip2 Complexes: Plasmids pA (coding for the luciferase reporter gene) and RSVLuc (coding for the luciferase reporter gene under the control of viral expression promotor RSV) were formulated with Lip2 in the following way. The requisite plasmid DNA was diluted from a stock solution to a concentration of 20 µg/ml in 150 mM sodium chloride; 25 mM HEPES, pH 7.4 or 0.6M sodium chloride; 25 mM HEPES, pH 7.4 (this buffer is called HBS). The solution was transferred to a 24 well culture dish and agitated on a shaker at 500 rpm. An equal volume of the Lip2 at a concentration of 26 µg/ml was then added to the DNA solution at a rate of 0.1 vol/min. After 1 h at room temperature the complexes were available for assay. 2.5 µg of DNA were used for each assay point.

Insulin Conjugate Complexes: Plasmids pB (coding for the transactivator) and RSVLuc were formulated with the insulin conjugate were diluted from stock solutions in HBS to a concentration of 100 µg/ml conjugate and 25 µg/ml NBC1 in HBS containing 0.83M NaCl. The solutions were transferred to a 24 well culture dish and agitated on a shaker concentration of 1 mg/ml into the peptide/conjugate solution to a final concentration of 50 µg/ml in each well. After 1 h at room temperature the complexes were available for assay. 2.Sug of DNA were used for each assay point.

Jurkat cell transfection: Cells were harvested on the day of assay by centrifugation at 1200 rpm for 5 min at room temperature. The cell pellet was resuspended in phosphate buffered saline (PBS) and re-centrifuged. This operation was performed twice. The cell pellet was then suspended in RPMI 1640 (Gibco Ltd.) containing 1 mg/ml human serum albumin and 50 µg/ml human transferrin, 12 µM chloroquine and the requisite DNA transfection complex. The transfection is then allowed to proceed by incubating the cells at 37° C. for 4h. After this time the cells are harvested by centrifugation at 2000 rpm. The cells were then suspended in 1 ml of RPMI and re-centrifuged. Finally the cells were suspended in 1.5 ml RPMI containing 10% FBS. The culture plate was then incubated at 37° C. for 24 h in an atmosphere of 5% $CO_2$.

HepG2 and HeLa cell transfection: Cells were cultured in MEM (Sigma Ltd.) Containing 1% non essential amino acids (Sigma Ltd.) And 10% fetal bovine serum. 24 h before the assay cells were trypsinized and suspended. The cells were counted and $1 \times 10^6$ cells aliquotted into 6 well culture plates. The next day the cells which are adherent were washed twice with PBS and 1 ml of MEM containing 1 mg/ml human serum albumin. 50 µg/ml human transferrin, 12 µM chloroquine and the requisite DNA transfection complex(es) added. After 4 h at 37° C. the cells were rinsed with PBS and 2 ml of MEM (Sigma Ltd.) containing 1% non essential amino acids (Sigma Ltd.) And 10% fetal bovine serum added. The cells were then incubated for a further 24 h. The cells were then washed with PBS and 0.5 ml of Trypsin-EDTA solution (Sigma Ltd.) Was then added to each well and the cells suspended. After 5 minutes 2 ml of complete MEM medium were added to each well and the cells transferred to a centrifuge tube. The cells were then washed twice with PBS.

Assay for Luciferase Expression: The contents of each well in the culture dish were transferred to centrifuge tubes and the cells collected by centrifugation at 13000 rpm. The pellet was resuspended in 0.12 ml of Lysis Buffer (100 mM sodium phosphate, pH 7.8; 8 mM MgC12, 1 mM EDTA; 1% Triton X-100 and 15% glycerol) and agitated with a pipette. The lysate was centrifuged at 13000 rpm for 1 minute and the supernatant collected. 80 µl of the supernatant were transferred to a luminometer tube. The luciferase activity was then assayed using a Berthold Lumat L9501 luminometer. The assay buffer used was Lysis buffer containing 10 mM Luciferin and 100 mM ATP. Light produced by the luciferase is integrated over 4 sec and is described was relative light units (RLU). The data were converted to RLU/mg protein (protein concentration of the lysate having been determined in this case by the Microtitre Plate BioRAD Lowry Assay Kit (BioRad Ltd.

Figure 5:
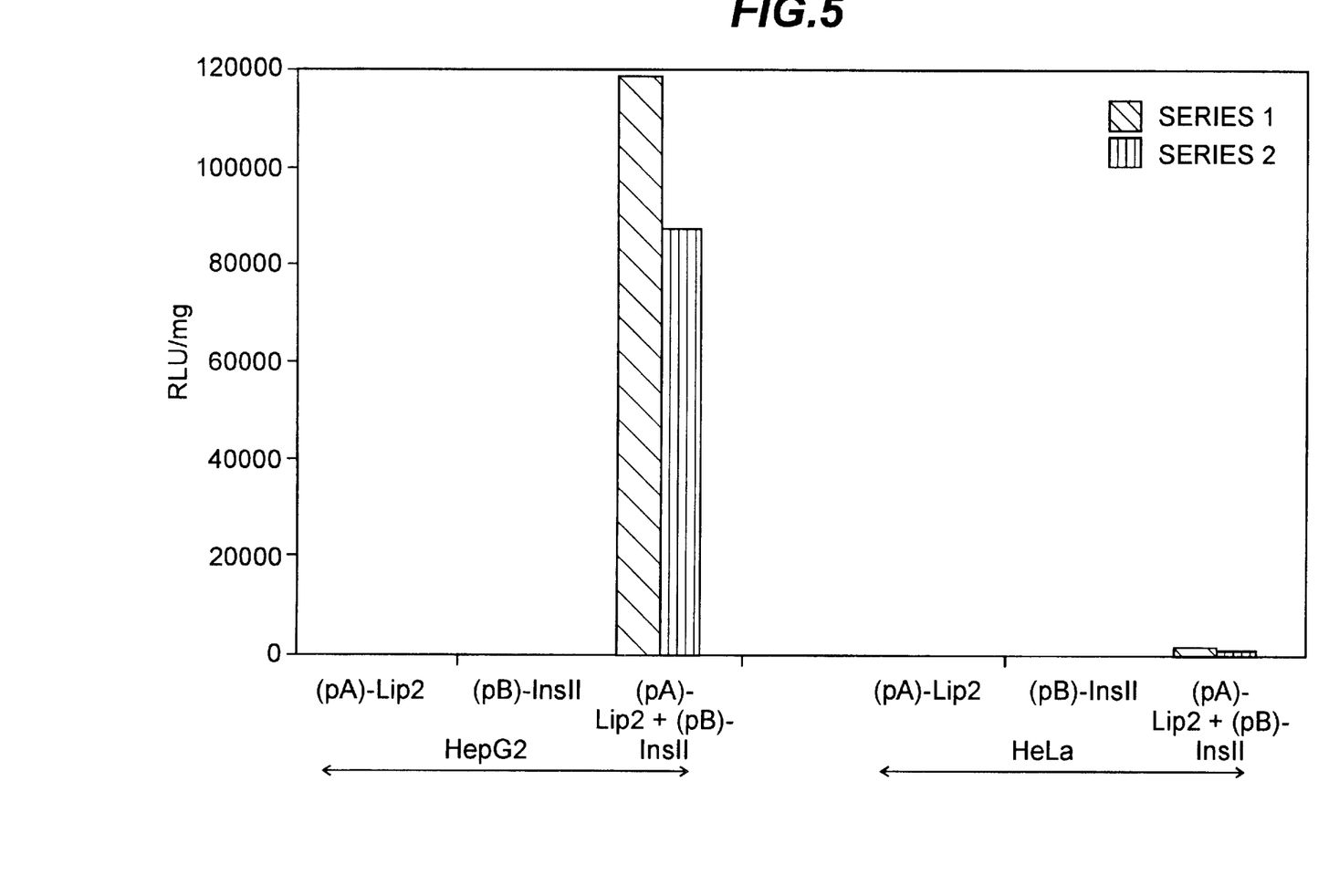
FIG. 5 presents results of an experiment described herein in which the InsII and Lip2 constructs are targeted to insulin receptor bearing HepG2 cells and to HeLa cells. Significant luciferase activity was found only when both constructs were delivered to HepG2 cells.
Figure 6:
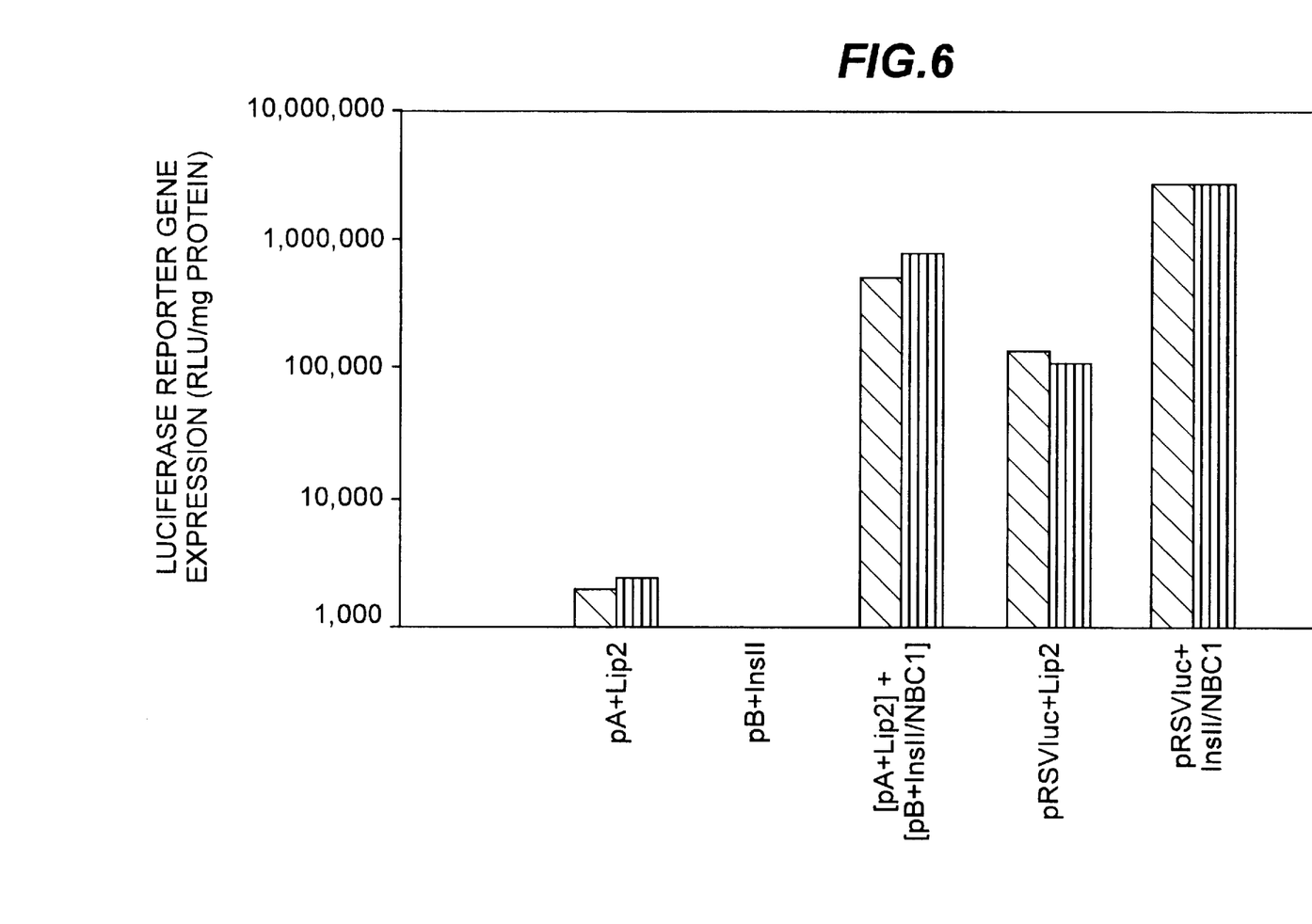
FIG. 6 is a histogram showing results of an experiment in which Jurkat cells are transfected with a Lip2 targeting complex containing plasmid pA (containing a luciferase reporter gene) and an insulin receptor targeting complex containing plasmid pB (coding for a transactivator of the luciferase gene). Relative efficiencies of delivery of each DNA was estimated using plasmid RSVluc, containing an unregulated luciferase reporter gene. Each set of two columns represents duplicate experiments.

In FIGS. 5 and 6, results are presented with respect to the above-described transfection of the cell lines.

FIG. 5 contains data demonstrating cell specific gene delivery and functional cooperation of the gene components of the effector system. Significant reporter gene activity was found only after incubation of the insulin receptor-bearing HepG2 cells with the InsII gene complex and the Lip2 gene complex. No significant reporter gene activity was found in either cell line when either of the InsII complex or the Lip2 complex was incubated alone with each cell line. In addition, no reporter gene activity was detected when both complexes were incubated with HeLa cells (which do not bear the insulin receptor).

The data in FIG. 6 shows that whenever each targeting complex alone, Lip2 or insulin receptor targeting complex, is used to transfect cells, no luciferase activity is produced, whereas when pRSVluc is carried along with either targeting complex, as a positive control, delivery of plasmid DNA is highly efficient (high levels of luciferase activity are produced), indicating that an incomplete expression system is present in the cells when each of Lip2 or the insulin receptor complex is present. However, when both targeting complexes are contacted with Jurkat cells, it is evident that both plasmids pA and pB are delivered to the cells, as near maximum xpected reporter gene expression is observed ((pA+Lip2)+(pB+InsII/NBC1)).

In the above system, the luciferase gene may be replaced by another reporter gene, for example, the CAT gene. CAT gene expression can be measured in the presence or absence or added tetracycline using procedures essentially as described by Wagner et al. (Wagner et al. PNAS (1992) 89, 7934–7938).

The insulin targeting system described herein may be tailored to deliver genes to and control gene expression in any cell expressing the insulin receptor. Examples are bone marrow stem cells, T-Cells, monocytes, macrophages, B-cells and other cells of the haemopoetic system. This invention also allows targeting to many other cells including tumor cells, liver cells and endothelial cells. Liver cells and monocytic cells are particularly amenable to this approach as they display high densities of insulin receptor molecules on their surface.

EXAMPLE 3

Heterodimer Formation and Targeted Functional Assembly of an MHC Antigen

The experimental rationale is based on the observation that many well characterised adhesion and lymphokine receptors of the immune system require the coexpression of two or more separate gene products in a single cell followed by post translational processing and assembly of a heterodimer at the cell surface for functional activity (see Springer, T., Nature (1990) 346, 425–434; Takeshita et al., Science (1992) 257, 379–383). Such systems form the basis of a two gene targeting system, based on the assembly of a functional protein heterodimer such as class II major histocompatibility antigens (MHC). Further levels of complexity can be built in using systems involving three or more vectors, using for example the assembly of a high affinity Il-2 receptor (three subunits) as a functional end point. Such systems are clearly not limited to the expression and functional assembly of membrane proteins, and may include for example intracellular proteins such as transcription factors.

Figure 4:
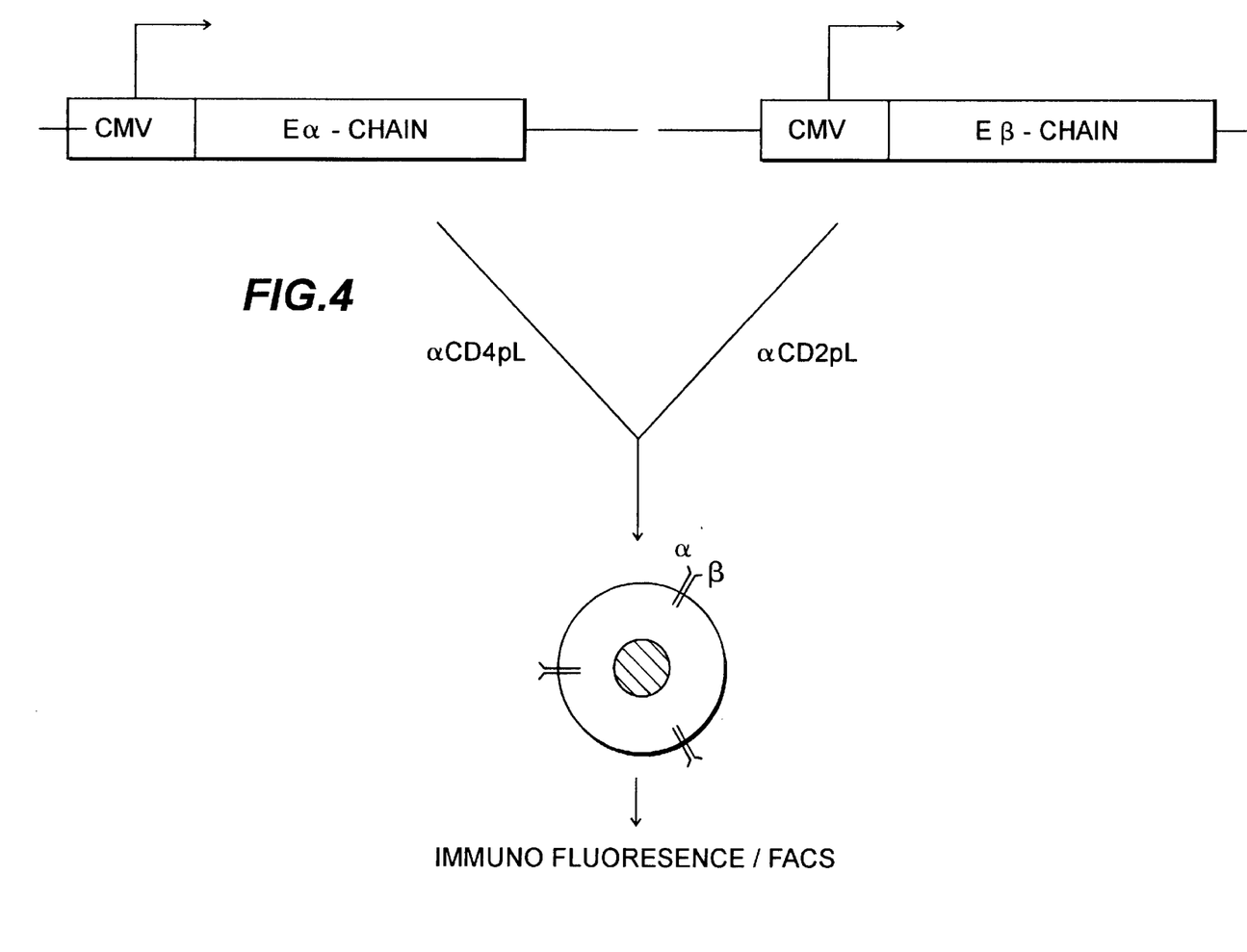

In these experiments the outcome is not dependent on the regulation of an gene by a regulator gene product, but the functional post-translational assembly of two or more gene products targeted using different ligand targeting complexes to a common cell type. For the example in question (see FIG. 4), one vector will comprise a promoter driving the expression of a first required gene product (subunit α), and the other a promoter driving the expression of a second required gene product (subunit β). Thus the a subunit vector DNA is mixed with ligand A' polylys and influenza peptide polylys as described by Wagner et al., (Wagner et al. PNAS (1992) 89, 7934–7938), to form a receptor mediated DNA targeting complex. Separately the β subunit vector DNA is mixed with Ligand B' polylys and the influenza peptide polylys to form another receptor mediated DNA targeting complex. The targeting complexes are then used to validate the two gene targeting system using three cell lines: cell-line Z which expresses markers A and B, cell-line X which expresses marker A but not marker B, and cell-line Y which expresses marker B but not marker A.

Evidence for functional αβ chain assembly in all three cell lines as a result of addition of the ligand A' gene complex or the ligand B' regulator gene complex alone or in combination to each cell-line using procedures essentially as described by Wagner et al., (Wagner et al., PNAS (1992) 89,7934–7938) may be determined by immunofluorescence essentially as described by James et al., Immunology (1991) 72, 213–218.

No functional assembly will be measurable over background when either the ligand A' or B' targeting complex are incubated alone with cell-lines X, Y, or Z. No functional assembly will be observed when ligand targeting complexes A' and B' are incubated together in the presence or absence of estrogen with cell-lines X or Y. However functional assembly of the αβ MHC complexes may be observed when ligand targeting complexes A' and B' are incubated together with cell-line Z.

This approach will demonstrate the successful targeting to and functional expression of both gene constructs to cell-line Z which carries markers A and B, and the absence of gene expression in cell-lines X and Y, which carry a single marker, A or B respectively.

EXAMPLE 4
Treatment of X-Linked-Gamma-Globulinemia According to the Invention

Diseases stemming from a genetic deficiency or defect are also treatable acording to the invention. One example of such a disease is X-linked-gamma-globulinemia. Targeting complexes according to the invention may be used to treat X-linked-gamma-globulinemia by introducing nucleic acid containing the Bruton's tyrosine kinase gene (Vetrie et al., 1993, Nature 361:226–233), which is carried on a 2.1 kb fragment delineated by the PvuI site at position (+33) and the HindIII site at position (+2126). If desired, the DNA also may include sequences which confer position independent, tissue specific gene expression, as taught in PCT/GB88/00655. The therapeutic gene also may encode a splice site and poly A tail, which may include portions of the human beta globin locus splice and poly A signals; i.e., a BamHI XbaI 2.8 kb 31 splice/poly A flanking sequence containing exon 2 IVSII—exon 3—poly A sequences. Briefly, DNA containing the Bruton's tyrosine kinase gene may be introduced directly into a patient for in vivo gene therapy or into pre-B cells for ex vivo therapy, as described in Martensson et al.; Eur. Jour. Immunol. 1987, 17:1499; Okabe et al., Eur. Jour. Immunol. 1992, 22:37; and Banerji et al., Cell 33:729, 1983, and administering the transfected pre-B cells into a patient afflicted with X-linked-gamma-globulinemia. A targeting complex for treatment of X-linked-gamma-globulinemia will include a ligand for targeting a preB cell. Such ligands are well-known in the art and will be specific for and capable of targeting one of the preB cell surface markers. As used herein, a "pre-B cell" refers to an immune system cell as defined in The Leukocyte Antigen Fact Book, 1993, Barclay et al., Eds., Academic Press, Harcourt Brace, London. A pre-B cell is thus defined by Barclay et al. as possessing the following cellular markers: scal, CD9, CD10, CD19, CD20, CD22, CD24, CD38, CD40, CD72, and CD74 (see A.T.C.C. catalog on hybridomas for cell lines producing such antibodies). For example, a preB cell may be specifically targeted in a pool of B cells without targeting lymphoid stem cells, mature B cells or plasma cells, using a first targeting ligand that is specific for the preB cell surface antigen scal (HB215) and a second targeting ligand that is specific for the preB cell surface antigen CD38 (OKT10, CRL 8022).

EXAMPLE 5
Treatment of Gaucher's Disease According to the Invention

Another example of a disease stemming from a genetic deficiency or defect is Gaucher's disease. The effector system described herein also may be used for treatment of Gaucher's disease. Gaucher's disease stems from one of two different genetic mutations. Gaucher's type 1 is a CGG - - >CAG mutation, which results in an Arg - - >Gln substitution at position 119 of the alpha-glucocerebrosidase polypeptide (Graves, DNA 7:521, 1988). Gaucher's type 2 is a CTG - >CCG mutation, which results in a Leu - - >Pro substitution at position 444 of the polypeptide (Tsuji, NEJM 316:570, 1987). The presence of a alpha-glucocerebrosidase gene encoding a wild type polypeptide is believed to substantially correct Gaucher's disease. Therefore, a therapeutic nucleic acid useful according to the invention includes the alpha-glucocerebrosidase gene, as described in Horowitz et al., 1989, Genomics 4:87–96, which is carried, as disclosed in Horowitz et al., on a 9722 base pair fragment extending from a BamHI site in exon 1 to an EcoRV site 31 to polyadenylation site. This fragment contains 11 exons and all intervening sequences, with translational start in exon 2. Sequences conferring position-independent and tissue-specific gene expression may be included in the construct and are carried on an 11.8 kb XhoI—SacI fragment from pIII.1yx construct as described in Bonifer et al., 1990, Euro. Mol. Biol. Org. Jour. 9;2843.

A targeting complex containing the alpha-glucocerebrosidase gene is used to treat Gaucher's disease by introducing the targeting complex directly into the host for in vivo treatment, or into isolated macrophages for ex vivo therapy, as described in Immunology and Cell Biology, 1993, Vol. 71, pages 75–78 and introducing the transfected macrophages into a patient afflicted with Gaucher's disease. Expression of the wild type transgene in a patient afflicted with Gaucher's disease should result in correction of the diseased state. The targeting complex will contain a ligand that specifically targets a cell surface antigen on a macrophage. Such ligands are well-known in the art, for example, a monoclonal antibody having specificity for and capable of targeting one or more of the macrophage cell surface markers. As used herein, a "macrophage" refers to an antigen presenting, phagocytic cell as defined in *The Leukocyte Antigen Fact Book,* 1993, Barclay et al., Eds., Academic Press, Harcourt Brace, London. That is, a macrophage is defined in Barclay et al. as including the following cell surface markers: CD14, CD16, CD26, CD31, CDw32, CD36, CD45RO, CD45RB, CD63, CD71, CD74, CD23, CD25 and CD69 (see A.T.C.C. catalog on hybridomas for cell lines producing such antibodies). For example, targeting ligands useful for targeting human macrophages may include one of the antibodies that are specific for macrophage cell surface antigen, such as 10B9 (ATCC HB172), 14E5 (ATCC HB174), 3C10 (ATCC TIB228), in combination with a second targeting ligand useful for targeting a macrophage subpopulation bearing the MAC-2 antigen (antibody TIB166) or the MAC-3 antigen (antiobdy TIB168).

For the above-described treatment of X-linked-gamma-globulinemia and Gaucher's Disease, a second targeting complex containing a regulator gene, e.g., encoding a transcriptional activator or repressor, the transcriptional regulator having target specificity for the transcription unit of the structural gene. Such regulators include those specific regulators described herein above, or additional regulators which are well-known in the art, including small molecules such as steroid hormones and their analogues, antibiotics, immunosuppressants, and other organic compounds (Furth et al., 1994, Proc. Natl. Acad. Sci. 91:9032; Spencer et al., 1993, Science 262:1079; Wang et al., 1994, Proc. Natl. Acad. Sci. 91:8180). In this way, expression of the structural gene is dependent upon the presence in the cell of the regulator molecule.

Pharmaceutical Formulation

The targeting ligand and plasmid DNA may be formulated separately for parenteral administration or as the transfection complex. In the latter case the transfection complex may be assembled just prior to use. In the case of a pharmaceutical composition the plasmid DNA of one of the vectors would contain a gene whose expression would have some beneficial effect on the cells of the recipient.

The targeting ligand and DNA may be exchanged into isotonic phosphate free buffer and sterile filtered through a 0.45 or $0.22\mu$ filter. The formulated solutions or transfection complexes ( a mixture of the delivery vehicle plasmid DNA) may be sterile filtered and aliquoted into suitable vials. The vials may be stored at 4° C., 20° C. or 80° C. or alternatively the DNA, delivery vehicle or transfection complex may be freeze dried form a buffer containing an appropriate carrier and bulking agent. In these cases the dosage form is reconstituted with a sterile solution before administration.

Use of this type of pharmaceutical composition in vivo or ex vivo with nucleic acid containing a gene of physiological importance, such as replacement of a defective gene or an additional potentially beneficial gene function, would be expected to bring about long term genetic modification of the cells and be effective in the treatment of disease.

Dosage and Mode of Administration

The targeting complexes of the invention will be administered using any suitable route. Further Modifications, such as pegylation which might increase the half-life of the vectors before uptake by the target cells, may be included. The complexes may be provided together as a single composition or in the form of separate compositions for simultaneous separate or sequential use.

For optimal efficiency of delivery of a therapeutic gene to a target cell, it is preferred that the nucleic acid containing the therapeutic gene, in condensed form, be less than about 100 nm, i.e., in the size range of approximately 1–100 nm, or less than approximately 50 kb in length.

Use of the effector system described herein in vivo or ex vivo with nucleic acid containing a gene of physiological importance, such as replacement of a defective gene or an additional potentially beneficial gene function, is expected to confer long term genetic modification of the cells and be effective in the treatment of disease.

For example, a patient that is subject to a viral or genetic disease may be treated in accordance with the invention via in vivo or ex vivo methods. For example in in vivo treatments, targeting complexes of the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective amount" will be determined by the level of enhancement of function of the transferred genetic material balanced against any risk or deleterious side effects. Monitoring levels of gene introduction, gene expression and/or the presence or levels of the encoded anti-viral protein will assist in selecting and adjusting the dosages administered. Generally, a composition including a targeting complex will be administered in a single dose in the range of 10 ng–100 ug/kg body weight, preferably in the range of 100 ng–10 ug/kg body weight, such that at least one copy of each of the therapeutic gene and the regulator gene is delivered to each target cell. The therapeutic gene will, of course, be associated with appropriate target regulatory sequences for expression of the gene in the target cell under control of regulator.

Ex vivo treatment is also contemplated within the present invention. Cell populations can be removed from the patient or otherwise provided, transduced with a therapeutic gene in accordance with the invention, then reintroduced into the patient, e.g., by intravenous or subcutaneous injection. In general, ex vivo cell dosages will be determined according to the desired therapeutic effect balanced against any deleterious side-effects. Such dosages will usually be in the range of $10^5$–$10^8$ cells per patient, daily weekly, or intermittently; preferably $10^6$–$10^7$ cells per patient.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

I claim:

1. A composition for producing a desired biological activity in a host cell, comprising a plurality of targeting complexes comprising a first targeting complex comprising a ligand which targets a first cell surface marker of a host cell and a first component of an effector system, and a second targeting complex comprising a second ligand which targets a second cell surface marker of a host cell and a second component of the effector system, wherein said second cell surface marker is different from said first cell surface marker, wherein selective internalization and functional cooperation of the components of the effector system results in said biological activity.

2. The composition of claim 1, said plurality further comprising a third targeting complex comprising a third ligand which targets a third cell surface marker of a host cell and a third component of the effector system, wherein said third cell surface marker is different from said first and said second cell surface markers, wherein selective internalization and functional cooperation of the components of said effector system results in said biological activity.

3. The composition of claim 1 wherein the effector system elicits the desired biological activity in the target cell only if all the components of the effector system found in the plurality of targeting complexes are internalized by the target cell and functionally cooperate therein.

4. The composition of claim 1 wherein the desired biological activity is elicited in the target cell by the selective internalization of the components found in the plurality of targeting complexes such that one component is specifically excluded from the target cell.

5. The composition of claim 1 wherein the components of the effector system comprise an effector transcription unit and a regulator which modulates the expression of the effector transcription unit.

6. The composition of claim 1, said effector transcription unit comprising a structural gene encoding an effector protein.

7. The composition of claim 5 wherein said regulator comprises a transcription unit, the presence of which regulates the effector transcription unit.

8. The composition of claim 7 wherein said regulator comprising a transcription unit comprises a gene encoding a regulatory protein which modulates expression of the effector transcription unit.

\* \* \* \* \*